US010080620B2

(12) United States Patent
Tennican et al.

(10) Patent No.: US 10,080,620 B2
(45) Date of Patent: Sep. 25, 2018

(54) PORTABLE MEDICAL DEVICE PROTECTORS

(71) Applicant: Hyprotek, Inc., Spokane, WA (US)

(72) Inventors: Patrick O. Tennican, Spokane, WA (US); L. Myles Phipps, Shelton, WA (US)

(73) Assignee: Hyprotek, Inc., Spokane, WA (US)

( * ) Notice: Subject to any disclaimer, the term of this patent is extended or adjusted under 35 U.S.C. 154(b) by 0 days.

(21) Appl. No.: 15/482,435

(22) Filed: Apr. 7, 2017

(65) Prior Publication Data

US 2017/0209229 A1    Jul. 27, 2017

Related U.S. Application Data

(63) Continuation of application No. 13/757,381, filed on Feb. 1, 2013, now abandoned.
(Continued)

(51) Int. Cl.
| B65D 81/24 | (2006.01) |
| A61B 50/33 | (2016.01) |
| A61M 25/00 | (2006.01) |
| A61B 50/20 | (2016.01) |
| B65D 81/26 | (2006.01) |
| B65D 33/28 | (2006.01) |
| B65D 33/25 | (2006.01) |
| A61B 50/30 | (2016.01) |

(52) U.S. Cl.
CPC ............. *A61B 50/33* (2016.02); *A61B 50/20* (2016.02); *A61M 25/002* (2013.01); *B65D 33/25* (2013.01); *B65D 33/28* (2013.01); *B65D 81/26* (2013.01); *A61B 2050/314* (2016.02)

(58) Field of Classification Search
CPC ...................... A61B 50/33; A61B 2050/3008; A61F 2/0095
USPC ................ 206/205, 210, 363–370, 438, 564, 206/570–572
See application file for complete search history.

(56) References Cited

U.S. PATENT DOCUMENTS 3,607,760 A    9/1971  McIntyre
3,851,649 A *  12/1974 Villari ................. A61M 25/002
                                                      206/223
(Continued)

FOREIGN PATENT DOCUMENTS

CA    2656491    11/2014
CN    2511272    9/2002
(Continued)

OTHER PUBLICATIONS

Translated Chinese Office Action dated Jun. 14, 2017 for Chinese Patent Application No. 201380006373.3, a counterpart foreign application of U.S. Appl. No. 13/757,423, 12 pages.
(Continued)

*Primary Examiner* — Luan K Bui
(74) *Attorney, Agent, or Firm* — Lee & Hayes, PLLC

(57) ABSTRACT

This disclosure describes example portable medical device protectors that may be used in combination with various antimicrobial and/or antiseptic agents to reduce contaminants on a portable medical device. According to some embodiments, the disclosure describes that the protectors may comprise an impermeable container to store a permeable applicator impregnated with an antimicrobial or antiseptic agent.

6 Claims, 4 Drawing Sheets

Related U.S. Application Data

(60) Provisional application No. 61/595,635, filed on Feb. 6, 2012.

(56) References Cited

U.S. PATENT DOCUMENTS

| | | | |
|---|---|---|---|
| 3,860,348 A | 1/1975 | Doyle | |
| 4,188,234 A | 2/1980 | Budnick | |
| 4,291,697 A | 9/1981 | Georgevich | |
| 4,440,207 A | 4/1984 | Genatempo et al. | |
| 4,446,967 A | 5/1984 | Halkyard | |
| 4,564,010 A | 1/1986 | Coughlan et al. | |
| 4,588,400 A | 5/1986 | Ring et al. | |
| 4,696,393 A | 9/1987 | Laipply | |
| 4,811,847 A | 3/1989 | Reif et al. | |
| 4,813,210 A | 3/1989 | Masuda et al. | |
| 4,830,856 A | 5/1989 | Peppers | |
| 4,893,956 A | 1/1990 | Wojcik et al. | |
| 4,954,239 A * | 9/1990 | Mueller | A61M 3/0262 |
| | | | 206/210 |
| 5,009,652 A | 4/1991 | Morgan et al. | |
| 5,015,228 A | 5/1991 | Columbus et al. | |
| 5,041,264 A | 8/1991 | Williams | |
| 5,046,608 A | 9/1991 | Laipply | |
| 5,171,523 A | 12/1992 | Williams | |
| 5,438,984 A | 8/1995 | Schoendorfer | |
| 5,454,798 A | 10/1995 | Kubalak et al. | |
| 5,554,135 A | 9/1996 | Menyhay | |
| 5,556,375 A | 9/1996 | Ewall | |
| 5,569,207 A | 10/1996 | Gisselberg et al. | |
| 5,637,080 A | 6/1997 | Geng | |
| 5,713,842 A | 2/1998 | Kay | |
| 5,716,636 A | 2/1998 | Horstmann et al. | |
| 5,730,530 A | 3/1998 | Stoddard et al. | |
| 5,732,716 A | 3/1998 | Utecht | |
| 5,772,031 A * | 6/1998 | Landis | A61B 50/30 |
| | | | 206/438 |
| 5,779,053 A | 7/1998 | Partika et al. | |
| 5,846,559 A | 12/1998 | Hopp | |
| 5,973,221 A | 10/1999 | Collyer et al. | |
| 6,063,029 A | 5/2000 | Saita et al. | |
| 6,071,541 A | 6/2000 | Murad | |
| 6,168,800 B1 | 1/2001 | Dobos et al. | |
| 6,274,232 B1 | 8/2001 | Otten et al. | |
| 6,455,066 B1 | 9/2002 | Fischer et al. | |
| 6,769,546 B2 * | 8/2004 | Busch | A61B 17/3401 |
| | | | 206/366 |
| 7,118,545 B2 | 10/2006 | Boyde | |
| 7,282,186 B2 | 10/2007 | Lake, Jr. et al. | |
| 7,478,962 B2 | 1/2009 | De Laforcade | |
| 7,482,021 B1 | 1/2009 | Tison et al. | |
| 7,762,044 B2 | 7/2010 | Clarke et al. | |
| 7,770,726 B2 | 8/2010 | Murray et al. | |
| 7,780,794 B2 | 8/2010 | Rogers et al. | |
| 7,799,010 B2 | 9/2010 | Tennican | |
| 8,065,773 B2 | 11/2011 | Vaillancourt et al. | |
| 8,273,303 B2 | 9/2012 | Ferlic et al. | |
| 8,336,152 B2 | 12/2012 | Vaillancourt et al. | |
| 8,486,004 B1 | 7/2013 | Propp | |
| 8,496,625 B2 | 7/2013 | Brugger et al. | |
| 8,647,326 B2 | 2/2014 | Solomon et al. | |
| 8,777,504 B2 | 7/2014 | Shaw et al. | |
| 8,778,387 B2 | 7/2014 | Tennican et al. | |
| 8,846,008 B2 | 9/2014 | Tennican et al. | |
| 9,522,001 B2 * | 12/2016 | Bui | A61B 17/06114 |
| 2002/0185406 A1 * | 12/2002 | Massengale | A61M 5/002 |
| | | | 206/571 |
| 2003/0007939 A1 | 1/2003 | Murad | |
| 2003/0138479 A1 | 7/2003 | Mizota et al. | |
| 2004/0037789 A1 | 2/2004 | Moneuze et al. | |
| 2004/0050402 A1 | 3/2004 | D'Auria | |
| 2004/0110841 A1 | 6/2004 | Kite et al. | |
| 2004/0129581 A1 * | 7/2004 | Tompkins | A61K 49/0409 |
| | | | 206/223 |
| 2005/0034731 A1 | 2/2005 | Rousseau et al. | |
| 2005/0084521 A1 | 4/2005 | Hamada et al. | |
| 2005/0107732 A1 | 5/2005 | Boyde | |
| 2005/0129897 A1 | 6/2005 | Zhou et al. | |
| 2005/0255172 A1 | 11/2005 | Omidbakhsh | |
| 2005/0265773 A1 | 12/2005 | De Laforcade | |
| 2006/0062834 A1 | 3/2006 | Dixon | |
| 2006/0129117 A1 | 6/2006 | Malowaniec | |
| 2006/0142684 A1 | 6/2006 | Shanbrom | |
| 2006/0151347 A1 | 7/2006 | Grossman | |
| 2006/0193816 A1 * | 8/2006 | Elfersy | A01N 33/12 |
| | | | 424/70.28 |
| 2007/0014685 A1 | 1/2007 | Halt, Sr. | |
| 2007/0034538 A1 * | 2/2007 | Landis | A61F 2/0095 |
| | | | 206/438 |
| 2007/0080017 A1 | 4/2007 | Stickley | |
| 2007/0179373 A1 | 8/2007 | Pronovost | |
| 2007/0246378 A1 | 10/2007 | Cheaure et al. | |
| 2007/0255193 A1 | 11/2007 | Patel et al. | |
| 2007/0274869 A1 | 11/2007 | Rannikko et al. | |
| 2008/0019889 A1 | 1/2008 | Rogers et al. | |
| 2008/0057136 A1 | 3/2008 | Polyakov et al. | |
| 2008/0063695 A1 | 3/2008 | Vitaris | |
| 2008/0119801 A1 | 5/2008 | Moore | |
| 2008/0181950 A1 | 7/2008 | Bates et al. | |
| 2009/0010998 A1 | 1/2009 | Marchitto et al. | |
| 2009/0012496 A1 | 1/2009 | Tennican | |
| 2009/0028750 A1 | 1/2009 | Ryan | |
| 2009/0036541 A1 | 2/2009 | Mardis | |
| 2009/0324508 A1 | 12/2009 | Bobbert | |
| 2010/0003067 A1 | 1/2010 | Shaw et al. | |
| 2010/0030170 A1 | 2/2010 | Keller et al. | |
| 2010/0050351 A1 | 3/2010 | Colantonio et al. | |
| 2010/0076362 A1 | 3/2010 | Utterberg et al. | |
| 2010/0078336 A1 | 4/2010 | Reyhan et al. | |
| 2010/0163435 A1 | 7/2010 | Fischer et al. | |
| 2010/0172794 A1 | 7/2010 | Ferlic et al. | |
| 2010/0240799 A1 * | 9/2010 | Hofmann | A61K 8/43 |
| | | | 523/122 |
| 2010/0260865 A1 | 10/2010 | Kritzler | |
| 2011/0052664 A1 | 3/2011 | Tennican et al. | |
| 2011/0184382 A1 | 7/2011 | Cady | |
| 2011/0265834 A1 | 11/2011 | Tennican | |
| 2011/0295207 A1 | 12/2011 | Brugger et al. | |
| 2012/0288571 A1 | 11/2012 | Tennican et al. | |
| 2013/0138085 A1 | 5/2013 | Tennican | |
| 2013/0287860 A1 | 10/2013 | Tennican et al. | |
| 2014/0243725 A1 | 8/2014 | Tennican et al. | |

FOREIGN PATENT DOCUMENTS

| | | |
|---|---|---|
| CN | 2546003 | 4/2003 |
| CN | 2705167 | 6/2005 |
| CN | 1711845 | 12/2005 |
| CN | 1813097 | 8/2006 |
| CN | 101279102 | 10/2008 |
| CN | 101505815 | 8/2009 |
| CN | 201481841 | 5/2010 |
| CN | 102133421 | 7/2011 |
| CN | 1039857988 | 7/2014 |
| EP | 0262792 | 4/1988 |
| EP | 1687039 | 1/2009 |
| FR | 2587207 | 3/1987 |
| GB | 3503843 | 6/1931 |
| JP | S34012395 | 8/1959 |
| JP | S34018480 | 11/1959 |
| JP | S36001593 | 1/1961 |
| JP | S53002302 | 1/1978 |
| JP | S58003476 | 7/1981 |
| JP | S59500801 | 5/1984 |
| JP | S61501019 | 5/1986 |
| JP | 02180278 | 7/1990 |
| JP | H02149225 | 12/1990 |
| JP | H05044111 | 6/1993 |
| JP | H07043749 | 9/1995 |
| JP | H08191855 | 7/1996 |
| JP | H08318975 | 12/1996 |
| JP | 10110268 | 4/1998 |
| JP | H10511999 | 11/1998 |
| JP | 2001510704 | 8/2001 |

(56) References Cited

FOREIGN PATENT DOCUMENTS

| JP | 2001525688 | 12/2001 |
|---|---|---|
| JP | 2002529545 | 9/2002 |
| JP | 2003277256 | 10/2003 |
| JP | 2004049540 | 2/2004 |
| JP | 2004351632 | 12/2004 |
| JP | 2005511147 | 4/2005 |
| JP | 2005120008 | 5/2005 |
| JP | 2005343566 | 12/2005 |
| JP | 2005350571 A | 12/2005 |
| JP | 2006503647 | 2/2006 |
| JP | 2006516003 | 6/2006 |
| JP | 2006232340 | 9/2006 |
| JP | 2006526664 | 11/2006 |
| JP | 2007044258 | 2/2007 |
| JP | 2007505093 | 3/2007 |
| JP | 07500751 | 8/2007 |
| JP | 2007536261 | 12/2007 |
| JP | 2008503485 | 2/2008 |
| JP | 2009519312 | 5/2009 |
| JP | 2009537250 | 10/2009 |
| JP | 2011056183 | 3/2011 |
| JP | 2011074014 | 4/2011 |
| JP | 2013503713 | 2/2013 |
| WO | WO8503275 | 8/1985 |
| WO | WO9204923 | 4/1992 |
| WO | WO9308777 | 5/1993 |
| WO | WO0156540 | 8/2001 |
| WO | WO2004091675 | 10/2004 |
| WO | WO2004108091 | 12/2004 |
| WO | WO2005003436 | 1/2005 |
| WO | WO2005025486 | 3/2005 |
| WO | WO2005062896 | 7/2005 |
| WO | WO2005089341 | 9/2005 |
| WO | WO2006009853 | 1/2006 |
| WO | WO2006/089139 A2 | 8/2006 |
| WO | WO2007068938 | 6/2007 |
| WO | WO2007137056 | 11/2007 |
| WO | WO2008003779 | 1/2008 |
| WO | WO2008009925 | 1/2008 |
| WO | WO2008063648 | 5/2008 |
| WO | WO2009076718 | 6/2009 |
| WO | WO2009136957 | 11/2009 |
| WO | WO2010128554 | 11/2010 |
| WO | WO2010131253 | 11/2010 |
| WO | WO2011028965 | 3/2011 |
| WO | WO2011019132 | 7/2011 |
| WO | WO2011091322 | 7/2011 |
| WO | WO2011163124 | 12/2011 |
| WO | WO2012007929 | 1/2012 |
| WO | WO2013082187 | 6/2013 |
| WO | WO2014025994 | 2/2014 |

OTHER PUBLICATIONS

The European Office Action dated May 30, 2017 for European Patent Application No. 13746984.7, a counterpart foreign application of U.S. Pat. No. 9,192,443, 3 pages.
Translated Japanese Office Action dated May 9, 2017 for Japanese Patent Application No. 2014-555816, a counterpart foreign application of U.S. Pat. No. 9,039,967, 7 pages.
Non-Final Office Action for U.S. Appl. No. 13/757,423, dated May 19, 2017, Patrick O. Tennican, "Adhesive Patch with Antimicrobial Composition", 14 pages.
Office action for U.S. Appl. No. 14/271,365, dated Feb. 22, 2016, Tennican et al., "Antimicrobial Medical Dressings and Protecting Wounds and Catheter Sites", 13 pages.
The Australian Office Action dated Nov. 4, 2013 for Australian patent application No. 2010289415, a counterpart foreign application of U.S. Appl. No. 12/874,188, 3 pages.
The Australian Office Action dated Nov. 16, 2015 for Australian patent application No. 2013217602, a counterpart foreign application of U.S. Pat. No. 9,039,967, 3 pages.

The Australian Office Action dated Nov. 24, 2016 for Australian patent application No. 2013217606, a counterpart foreign application of U.S. Appl. No. 13/757,423, 3 pages.
The Australian Office Action dated Nov. 30, 2015 for Australian patent application No. 201321760, a counterpart foreign application of U.S. Appl. No. 13/757,381, 3 pages.
The Australian Office Action dated Feb. 3, 2017 for Australian Patent Application No. 2013217607, a counterpart foreign application of U.S. Pat. No. 9,192,443, 4 pages.
The Australian Office Action dated Mar. 13, 2014 for Australian patent application No. 2011207398, a counterpart foreign application of U.S. Appl. No. 13/554,962, 3 pages.
The Australian Office Action dated Jul. 21, 2016 for Australian Patent Application No. 2013217602, a counterpart foreign application of U.S. Pat. No. 9,039,967, 4 pages.
The Australian Office Action dated Sep. 29, 2016 for Australian patent application No. 2013217607, a counterpart foreiign application of U.S. Pat. No. 9,192,443, 4 pages.
The Canadian Office Action dated Jan. 12, 2017 for Canadian patent application No. 2786380, a counterpart foreign application of U.S. Pat. No. 8,846,008, 4 pages.
The Canadian Office Action dated Nov. 8, 2016 for Canadian patent application No. 2772042, a counterpart foreign application of U.S. Pat. No. 8,778,387, 3 pages.
Carson, "Local Anesthetics That Metabolize to 2,6-Xylidine or o-Toluidine," Integrated Laboratory Systems, Oct. 2000, 329 pages.
Translated Chinese Office Action dated Jan. 26, 2016 for Chinese Patent Application No. 201380006373.3, a counterpart foreign application of U.S. Appl. No. 13/757,423, 16 pages.
Translated Chinese Office Action dated Jan. 26, 2017 for Chinese Patent Application No. 201380007893.6, a counterpart foreign application of U.S. Pat. No. 9,039,967, 12 pages.
Translated Chinese Office Action dated Oct. 17, 2013 for Chinese patent application No. 201180006632.3, a counterpart foreign application of U.S. Appl. No. 13/554,962, 13 page.
Translated Chinese Office Action dated Oct. 18, 2016 for Chinese patent application No. 201380006373.3, a counerpart foreign application of U.S. Appl. No. 13/757,423, 17 pages.
Translated Chinese Office Action dated Oct. 23, 2014 for Chinese patent application No. 201080047665.8, a counterpart foreign application of U.S. Pat. No. 8,778,387, 13 pages.
Translated Chinese Office Action dated Nov. 27, 2015 for Chinese patent application No. 201380007894.0, a counterpart foreign application of U.S. Appl. No. 13/757,381, 18 pages.
Translated Chinese Office Action dated Nov. 4, 2015 for Chinese patent application No. 201380008084.7, a counterpart foreign application of U.S. Pat. No. 9,192,443, 22 pages.
Translated Chinese Office Action dated Dec. 1, 2015 for Chinese patent application No. 201380007893.6, a counterpart foreign application of U.S. Pat. No. 9,039,967, 19 pages.
Translated Chinese Office Action dated Dec. 30, 2016 for Chinese patent application No. 201380007894.0, a counterpart foreign application of U.S. Appl. No. 13/757,381, 16 pages.
Translated Chinese Office Action dated Dec. 8, 2016 for Chinese Patent Application No. 201380008084.7, a counterpart foreign application of U.S. Pat. No. 9,192,443, 23 pages.
Translated Chinese Office Action dated Apr. 10, 2014 for Chinese patent application No. 201180006632.3, a counterpart foreign application of U.S. Appl. No. 13/554,962, 19 pages.
Translated Chinese Office Action dated Apr. 22, 2014 for Chinese patent application No. 201080047665.8, a counterpart foreign application of U.S. Appl. No. 12/874,188, 17 pages.
Translated Chinese Office Action dated Apr. 8, 2015 for Chinese patent application No. 201180006632.3, a counterpart foreign application of U.S. Pat. No. 8,846,008, 19 pages.
Translated Chinese Office Action dated Apr. 9, 2015 for Chinese patent application No. 201080047665.8, a counterpart foreign application of U.S. Pat. No. 8,778,387, 8 pages.
The Chinese Office Action dated Jun. 1, 2016 for Chinese Patent Application No. 201380008084.7, a counterpart foreign application of U.S. Pat. No. 9,192,443.

(56) References Cited

OTHER PUBLICATIONS

Translated Chinese Office Action dated Jun. 21, 2016 for Chinese Patent Application No. 201380007894.0, a counterpart foreign application of U.S. Appl. No. 13/757,381, 10 pages.
Translated Chinese Office Action dated Aug. 12, 2013 for Chinese patent application No. 201080047665.8, a counterpart foreign application of U.S. Appl. No. 12/874,188, 13 pages.
Translated Chinese Office Action dated Aug. 2, 2016 for Chinese patent application No. CN201380007893.6, a counterpart foreign applicaiton of U.S. Pat. No. 9,039,967, 20 pages.
Translated Chinese Office Action dated Sep. 25, 2014 for Chinese patent application No. 201180006632.3, a counterpart foreign application of U.S. Appl. No. 13/554,962, 19 pages.
The European Office Action dated Jan. 19, 2016 for European patent application No. 13746209.9, a counterpart foreign application of U.S. Pat. No. 9,039,967, 4 pages.
The European Office Action dated Oct. 7, 2016 for European Patent Application No. 13747071.2, a counterpart foreign application of U.S. Appl. No. 13/757,381, 4 pages.
The European Office Action dated Dec. 9, 2016 for European Patent Application No. 13746984.7, a counterpart foreiign application of U.S. Pat. No. 9,192,443, 4 pages.
The European Office Action dated Feb. 14, 2017 for European Patent Application No. 13747071.2, a counterpart foreign application of U.S. Appl. No. 13/757,381, 5 pages.
The European Office Action dated Mar. 24, 2017 for European Patent Application No. 10814534.3, a counterpart foreign application of U.S. Pat. No. 8,778,387, 4 pages.
The European Office Action dated Mar. 29, 2016 for European patent application No. 11701925.7, a counterpart foreign applcation of U.S. Pat. No. 8,846,008, 5 pages.
The European Office Action dated Mar. 30, 2016 for European patent application No. 13747071.2, a counterpart foreign application of U.S. Appl. No. 13/757,381 4 pages.
The European Office Action dated Jun. 3, 2016 for European Patent Application No. 13746209.9, a counterpart foreign application of U.S. Pat. No. 9,039,967, 4 pages.
The European Office Action dated Sep. 12, 2014 for European patent application No. 11701925.7, a counterpart foreign application of U.S. Pat. No. 8,846,008, 5 pages.
The European Search Report dated Apr. 23, 2014 for European patent application No. , 11 pages.
The Extended European Search Report dated Mo Sep. 10, 2015 for European Patent Application No. 13747071.2, 8 pages.
The Extended European Search Report dated Sep. 11, 2015 for European Patent Application 13746209.9, 6 pages.
The Extended European Search Report dated Sep. 17, 2015 for European patent application No. 13746984.7, 7 pages.
The Extended European Search Report dated Sep. 18, 2015 for European Patent Application No. 13746515.9, 7 pages.
Final Office Action for U.S. Appl. No. 13/554,962, dated Dec. 5, 2013, Patrick O. Tennican, "Antimicrobial Agents and Methods of Use", 14 pages.
Hospenthal et al., "Guidelines for the Prevention of Infections After Combat-Related injuries", Journal of Trauma Injury, Infection, and Critical Care, vol. 64, No. 3, Mar. 2008, pp. S211-S220.
Translated Japanese Office Action dated Oct. 25, 2016 for Japanese Patent Application No. 2016-000215, a counterpart foreign application of U.S. Pat. No. 8,846,008, 11 pages.
Translated Japanese Office Action dated Nov. 22, 2016 for Japanese Patent Application No. 2014-555816, a counterpart foreign application of U.S. Pat. No. 9,039,967, 14 pages.
Translated Japanese Office Action dated Jan. 31, 2017 for Japanese Patent Application No. 2014-555818, a counterpart foreign application of U.S. Appl. No. 13/757,381, 15 pages.
Translated Japanese Office Action dated Oct. 18, 2016 for Japanese Patent Application No. 2014-555822, a counterpart foreign application of U.S. Pat. No. 9,192,443, 13 pages.

Translated Japanese Office Action dated Oct. 25, 2016 for Japanese Patent Application No. 2014-555821, a counterpart foreign application of U.S. Appl. No. 13/757,423, 9 pages.
Translated Japanese Office Action dated Dec. 24, 2014 for Japanese patent application No. 2012-550177, a counterpart foreign application of U.S. Pat. No. 8,846,008, 4 pages.
Translated Japanese Office Action dated Feb. 28, 2017 for Japanese Patent Application No. 2014-555821, a counterpart foreign application of U.S. Appl. No. 13/757,423, 5 pages.
Translated Japanese Office Action dated Apr. 14, 2015 for Japanese patent application No. 2012-528071, a counterpart foreign application of U.S. Pat. No. 8,778,387, 9 pages.
Translated Japanese Office Action dated Aug. 11, 2015 for Japanese patent application No. 2012-550177, a counterpart foreign application of U.S. Pat. No. 8,846,008, 4 pages.
Translated Japanese Office Action dated Aug. 19, 2014 for Japanese patent application No. 2012-528071, a counterpart foreign application of U.S. Pat. No. 8,778,387, 10 pages.
Japanese Patent No. JP6501857, which corresponds to International Patent Publication No. WO92/04923.
The Korean Office Action dated Dec. 1, 2016 for Korean Patent Application No. 10-2012-7019446, a counterpart foreign application of U.S. Pat. No. 8,846,008.
McGee et al., "Preventing Complications of Central Venous Catheterization", The New England Journal of Medicine, vol. 348, No. 12, Mar. 20, 2003, pp. 1123-1133.
The Mexican Office Action dated Jul. 2, 2014 for Mexican patent application No. MX/a/2012/008482, a counterpart foreign application of U.S. Appl. No. 13/554,962, 2 pages.
The Mexican Office Action dated Jan. 13, 2015 for Mexican patent application No. MX/a/2012/002746, a counterpart foreign application of U.S. Pat. No. 8,778,387, 2 pages.
The Mexican Office Action dated Oct. 24, 2016 for Mexican patent application No. MX/a/2014/009435, a counterpart foreign application of U.S. Pat. No. 9,039,967.
The Mexican Office Action dated May 26, 2014 for Mexican patent application No. MX/a/2012/002746, a counterpart foreign application of U.S. Pat. No. 8,778,387, 4 pages.
Nouri-Nigjeh et al., "Lidocaine oxidation by electrogenerated reactive oxygen species in the light of oxidative drug metabolism," Electrochemistry in the Mimicry of Oxidative Drug Metabolism, 2010, pp. 43-64.
Office Action for U.S. Appl. No. 14/271,365, dated Feb. 3, 2017, Patrick O. Tennican, "Antimicrobial Medical Dressings and Protecting Wounds and Catheter Sites", 7 pages.
Office Action for U.S. Appl. No. 14/271,365, dated Jan. 23, 2015, Patrick O. Tennican, "Antimicrobial Medical Dressings and Protecting Wounds and Catheter Sites", 8 pages.
Final Office Action for U.S. Appl. No. 13/757,423, dated Oct. 27, 2015, Patrick O. Tennican, "Adhesive Patch with Antimicrobial Composition", 12 pages.
Office Action for U.S. Appl. No. 13/924,410, dated Nov. 22, 2013, Patrick O. Tennican, "Antimicrobial Agents and Methods of Use", 15 pages.
Office action for U.S. Appl. No. 13/757,381, dated Nov. 25, 2015, Tennican et al., "Portable Medical Device Protectors", 7 pages.
Non-Final Office Action for U.S. Appl. No. 13/757,423, dated Dec. 1, 2016, Patrick O. Tennican, "Adhesive Patch with Antimicrobial Composition", 22 pages.
Office Action for U.S. Appl. No. 13/757,381, dated Dec. 12, 2016, Tennican et al., "Portable Medical Device Protectors", 7 pages.
Final Office Action for U.S. Appl. No. 12/874,188, dated Dec. 19, 2012, Patrick O. Tennican et al., "Antimicrobial Medical Dressings and Protecting Wounds and Catheter Sites", 6 pages.
Non-Final Office Action for US Patent Application dated Feb. 15, 2013, Patrick O. Tennican et al., "Antimicrobial Agents and Methods of Use", 12 pages.
Non-Final Office Action for U.S. Appl. No. 12/874,188, dated Feb. 7, 2014, Patrick O. Tennican et al., "Antimicrobial Medical Dressings and Protecting Wounds and Catheter Sites", 6 pages.
Office Action for U.S. Appl. No. 13/757,465, dated Feb. 9, 2015, Patrick O. Tennican, "Combined Cap Applicators", 14 pages.

(56) References Cited

OTHER PUBLICATIONS

Office Action for U.S. Appl. No. 13/934,135, dated Mar. 12, 2015, Patrick O. Tennican, "Antimicrobial Agents and Methods of Use", 14 pages.
Office Action for U.S. Appl. No. 13/924,410, dated Mar. 28, 2014, Patrick O. Tennican, "Antimicrobial Agents and Methods of Use", 18 pages.
Office action for U.S. Appl. No. 13/757,381, dated Mar. 7, 2016, Tennican et al., "Portable Medical Device Protectors", 7 pages.
Non-Final Office Action for U.S. Appl. No. 13/757,423, dated Apr. 10, 2015, Patrick O. Tennican, "Adhesive Patch with Antimicrobial Composition", 13 pages.
Final Office Action for U.S. Appl. No. 13/757,465, dated May 28, 2015, Patrick O. Tennican, "Combined Cap Applicators", 15 pages.
Office action for U.S. Appl. No. 14/271,365, dated May 5, 2016, Tennican et al., "Antimicrobial Medical Dressings and Protecting Wounds and Catheter Sites", 9 pages.
Final Office Action for U.S. Appl. No. 14/271,365, dated Jun. 1, 2015, Patrick O. Tennican, "Antimicrobial Medical Dressings and Protecting Wounds and Catheter Sites", 10 pages.
Non-Final Office Action for U.S. Appl. No. 12/874,188, dated Jun. 29, 2012, Patrick O. Tennican et al., "Antimicrobial Medical Dressings and Protecting Wounds and Catheter Sites", 6 pages.
Office Action for U.S. Appl. No. 13/757,381, dated Jul. 1, 2015, Patrick O. Tennican, "Portable Medical Device Protectors", 9 pages.
Final Office Action for U.S. Appl. No. 13/934,135, dated Jul. 7, 2015, Patrick O. Tennican, "Antimicrobial Agents and Methods of Use", 9 pages.
Office action for U.S. Appl. No. 13/757,318, dated Aug. 26, 2017, Tennican, "Antiseptic Applicators and Packaging Techniques", 9 pages.
Office action for U.S. Appl. No. 12/874,188, dated Sep. 10, 2013, Tennican et al., "Antimicrobial Medical Dressings and Protecting Wounds and Catheter Sites", 6 pages.
Office action for U.S. Appl. No. 14/271,365, dated Sep. 11, 2014, Tennican et al., "Antimicrobial Medical Dressings and Protecting Wounds and Catheter Sites", 7 pages.
Office action for U.S. Appl. No. 13/757,423, dated Sep. 4, 2014, Tennican, "Adhesive Patch with Antimicrobial Composition", 13 pages.
Office Action for U.S. Appl. No. 14/271,365, dated Oct. 2, 2015, Patrick O. Tennican, "Antimicrobial Medical Dressings and Protecting Wounds and Catheter Sites", 9 pages.
PCT Search Report dated May 15, 2013 for PCT application No. PCT/US13/24635, 10 pages.
The PCT Search Report dated May 13, 2013 for PCT application No. PCT/US13/24644, 10 pages.
Tjhe PCT Search Report dated May 15, 2013 for PCT application No. PCT/US13/24651, 12 pages.
The PCT Search Report dated May 20, 2011 for PCT Application No. PCT/US10/47756.
The PCT Search report dated May 31, 2013 for PCT application No. PCT/US13/24649, 14 pages.
The PCT Search Report dated Aug. 1, 2011 for PCT application No. PCT/US11/22150.

Translated Russian Office Action dated Jan. 23, 2015 for Russian patent applcation No. 2012136147, a counterpart foreign application of US patent application No., pages.
Singhal et al., "Wound Infection", eMedicine from WebMD «http://www.emedicine,medscape,com», Updated Sep. 15, 2009, 32 pages.
"The Infection", vol. 28, No. 3, 1998, pp. 107-111 (Document in Japanese, translation not available).
"VERSENE Acid—Solubility", The Dow Chemical Company, Sep. 15, 2010, pp. 1-3.
"VERSENE NA Disodium EDTA Chelating Agent", The Dow Chemical Company, Oct. 2009, pp. 1-2.
The European Office Action dated May 3, 2017 for European Patent Application No. 13747071.2, a counterpart foreign application of U.S. Appl. No. 13/757,381, 4 pages.
Translated Japanese Office Action dated Mar. 28, 2017 for Japanese patent application No. 2014-555822, a counterpart foreign application of U.S. Pat. No. 9,192,443, 15 pages.
The Mexican Office Action dated Mar. 15, 2017 for Mexican patent application No. MX/a/2014/009435, a counterpart foreign application of U.S. Pat. No. 9,039,967.
The Canadian Office Action dated Aug. 16, 2017 for Canadian Patent Application No. 2772042, a counterpart foreign application of U.S. Pat. No. 8,778,387, 5 pages.
The European Office Action dated Jul. 21, 2017 for European Patent Application No. 13746515.9, a counterpart foreign application of U.S. Appl. No. 13/757,423, 7 pages.
The European Office Action dated Sep. 1, 2017 for European patent application No. EP13747071.2, a counterpart foreign application of U.S. Appl. No. 13/757,381, 4 pages.
The Indian Office Action dated Oct. 12, 2017 for Indian patent application No. 6488/DELNP/2012, a counterpart foreign application of U.S. Pat. No. 8,846,008, 6 pages.
Translated Japanese Office Action dated Jun. 20, 2017 for Japanese patent application No. 2014-555818, a counterpart foreign application of U.S. Appl. No. 13/757,381, 5 pages.
Translated Japanese Office Action dated Aug. 25, 2017 for Japanese Patent Application No. 2014-555821, a counterpart foreign application of U.S. Appl. No. 13/757,423, 9 pages.
The Japanes Office Action dated Sep. 4, 2017 for Japanese patent application No. 2014-555822, a counterpart foreign application of U.S. Pat. No. 9,192,443, 7 pages.
Translated Chinese Office Action dated Nov. 22, 2017 for Chinese Patent Application No. 201380007893.6, a counterpart foreign application of U.S. Pat. No. 9,039,967, 16 pages.
The Chinese Office Action dated Jul. 25, 2017 for Chinese patent application No. 201380007894.0, a counterpart foreign application of U.S. Appl. No. 13/757,381.
The European Office Action dated Jan. 30, 2018 for European patent application No. 13747071.2, a counterpart foreign application of U.S. Appl. No. 13/757,381, 3 pages.
The Japanese Office Action dated Nov. 14, 2017 for Japanese patent application No. 2014-555816, a counterpart foreign application of U.S. Pat. No. 9,039,967.
Translated copy of the Japanese Office Action dated Jul. 10, 2018 for Japanese patent application No. 2017-171461, a counterpart foreign application of U.S. Appl. No. 9,039,967, 17 pages.

* cited by examiner

PORTABLE MEDICAL DEVICE PROTECTORS

CROSS REFERENCE TO RELATED APPLICATION

This Application claims priority to and is a continuation of U.S. patent application Ser. No. 13/757,381 filed Feb. 1, 2013, entitled "Portable Medical Device Protectors," which claims priority to U.S. Provisional Patent Application No. 61/595,635 filed on Feb. 6, 2012 entitled "Antiseptic Applicators and Protective Devices," which are hereby incorporated by reference in their entirety.

BACKGROUND

Healthcare acquired infection (HAI) has been recognized as a significant cause of preventable mortality and morbidity. In the United States, HAI annually costs nearly 99,000 lives and billions of dollars in additional treatment and hospitalization. Klevens, et al., *Estimating Health Care-Associated Infection and Deaths in U.S. Hospitals*, 2002, Public Health Reports, Vol. 122, p. 160, 2007. Contamination of intravascular catheters, surgical sites and invasive procedure sites, frequently leads to device removal and replacement, prolonged parenteral antimicrobial therapy, and extended hospitalizations and rehabilitation.

The spread of multi-antimicrobial resistant organisms frequently are spread by healthcare providers' hands or medical equipment, from one colonized or infected patient to other susceptible patients. Surgical site infections may result from inadequate antiseptic preparations of the skin. Widespread use of chlorhexidine gluconate (CHG) for routine washing and wiping of pre-operative sites, has led to the increased incidence of resistant *Staphyloccus aureus*, both to methicillin (MRSA) and CHG, in some hospital environments.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Overview

Figure 1:
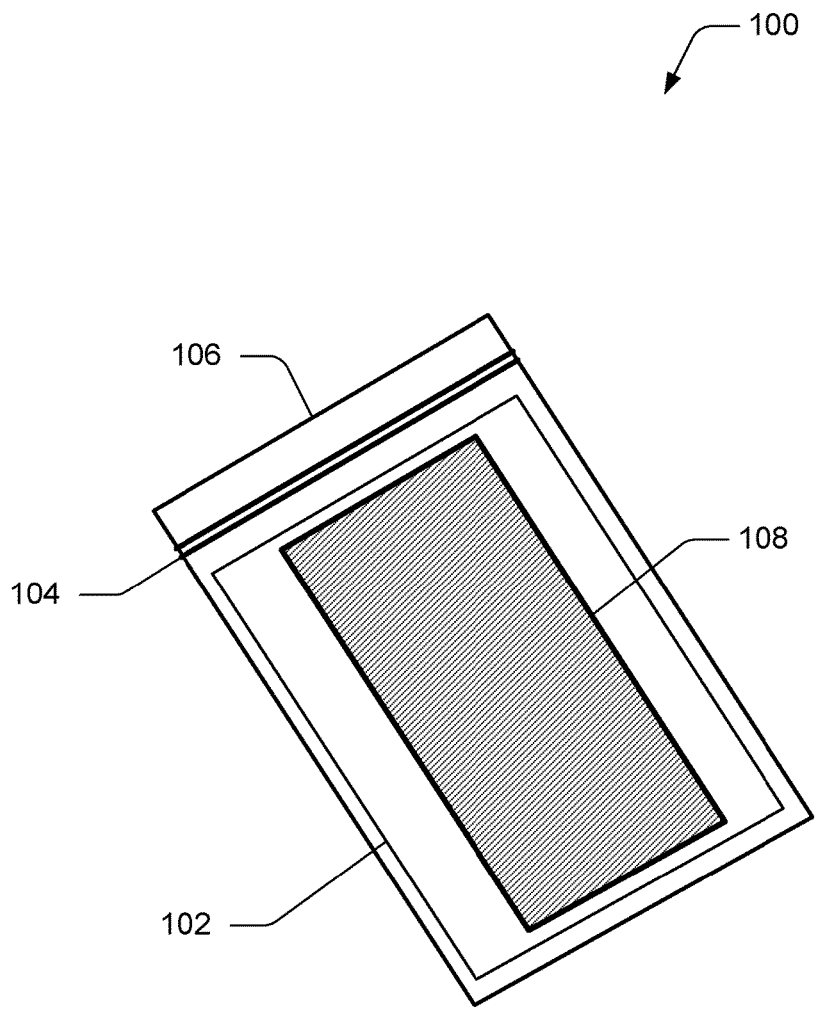
FIG. 1 illustrates an example portable medical device protector having a permeable applicator located within an impermeable container.

This disclosure describes medical applicators and protectors designed to reduce and/or prevent infections. In one embodiment, the disclosure describes a portable medical device protector comprising a sealable impermeable container or receptacle to hold a portable medical device (e.g., stethoscope) and a permeable, absorbent and/or adsorbent applicator carrying an antimicrobial or antiseptic composition. In some embodiments the antimicrobial composition may comprise water, a low molecular weight alcohol, a peroxide or peroxide-generating agent, and a chelating agent. In some embodiments, the permeable applicator may be used to wipe the portable medical device to prevent and/or reduce transmission of infection as the portable medical device is used or transported between multiple patients.

The detailed discussion below begins with a section entitled "Example Antimicrobial Composition", which describes in detail an example antimicrobial composition that may be included in the medical applicators and protectors described herein. The next section entitled "Example Device Protectors" describes example cleaning and protective devices for use of a portable medical device. Next, an "Example Process" for operating an example device protector is described. Finally, the disclosure concludes with a brief "Conclusion."

This overview, including section titles, is provided to introduce a selection of concepts in a simplified form that are further described below. The overview is provided for the reader's convenience and is not intended to limit the scope of the claims, nor the proceeding sections.

Example Antimicrobial Composition

In one example implementation, antimicrobial compositions that may be used in connection with the approaches described herein may include those described in, for example, International Patent Application No. PCT/US2011/022150, filed Jan. 21, 2011, to Tennican et al., and, U.S. Non-Provisional patent application Ser. No. 13/688,078, filed Nov. 28, 2012, to Tennican, which are incorporated herein by reference. For example, the antimicrobial compositions may include water ($H_2O$), a strong and non-toxic chelating agent such as ethylenediaminetetraacetic acid (EDTA) (e.g., disodium EDTA, calcium disodium EDTA, magnesium EDTA, potassium EDTA, gallium EDTA) or sodium citrate (or acids, salts, derivatives, or other forms of EDTA or sodium citrate), a short-chain monohydric alcohol (e.g., ethanol with a molecular formula of $C_2H_5OH$ and an empirical formula of $C_2H_6O$), and a strong, small molecule oxidizing agent such as hydrogen peroxide ($H_2O_2$). In one specific example, the compositions may consist essentially of water, EDTA, ethanol, and hydrogen peroxide. Additional ingredients can include thickeners, gellants, surfactants, foamers and/or foam stabilizers. However, in other examples, other antimicrobial compositions may be used in combination with the applicators and devices described in this disclosure.

The antimicrobial compositions may be in a liquid form or a gel form, and may be combined with one or more carriers or diluents, depending on the needs of a specific application. For example, if the antimicrobial composition is used as a cleaning agent the antimicrobial composition may be in a liquid form. In that case, the concentration of the various constituents may depend on, for example, a desired level of sanitation and/or disinfection, whether the composition is being applied directly to living tissue or to a medical device, and/or to avoid irritation of tissue to which the composition will be applied directly or indirectly (e.g., via a medical device to which the composition is or was applied).

In addition to providing disinfection at the time of the application, the antimicrobial compositions may also provide a lasting barrier against contamination. For example, even after volatile constituents of the composition (e.g., water, alcohol, hydrogen peroxide, etc.) have evaporated, the chelating agent may remain on the treated surfaces (e.g., multiple use vial or port cleaning/protecting device, stethoscope, fingers, surrounding tissue, etc.) as a barrier that will provide antibacterial, antifungal or sporicidal (e.g., preventing germination of the spores), anti-parasitic, spermicidal or spermiostatic (e.g., decrease the motility of spermatozoon) and antiviral qualities. By robbing the environment of components (e.g., iron, magnesium, and manganese) that are needed for the bacteria (e.g., *staphylococcus aureus* (MRSA), *Pseudomonas aeruginosa* and other resistant bacteria), spores, parasites, fungus, and viruses to reproduce, the chelating agent provides a lasting defense to contamination even after other constituents of the antimicrobial composition have evaporated. Furthermore, the hydrogen peroxide in the antimicrobial compositions may induce a charge on a surface of materials (e.g., silicone materials) to which the antimicrobial compositions are applied, which make the materials more resistant to bacteria or other microorganisms.

The antimicrobial composition described above may also provide a visual indication of contamination when applied to a surface or material, such indication may allow users to identify and clean surfaces to prevent infection.

The term "about" or "approximate" as used in context of describing the example antimicrobial composition is to be construed to include a reasonable margin of error that would be acceptable and/or known in the art.

Example Device Protectors

Figure 2:
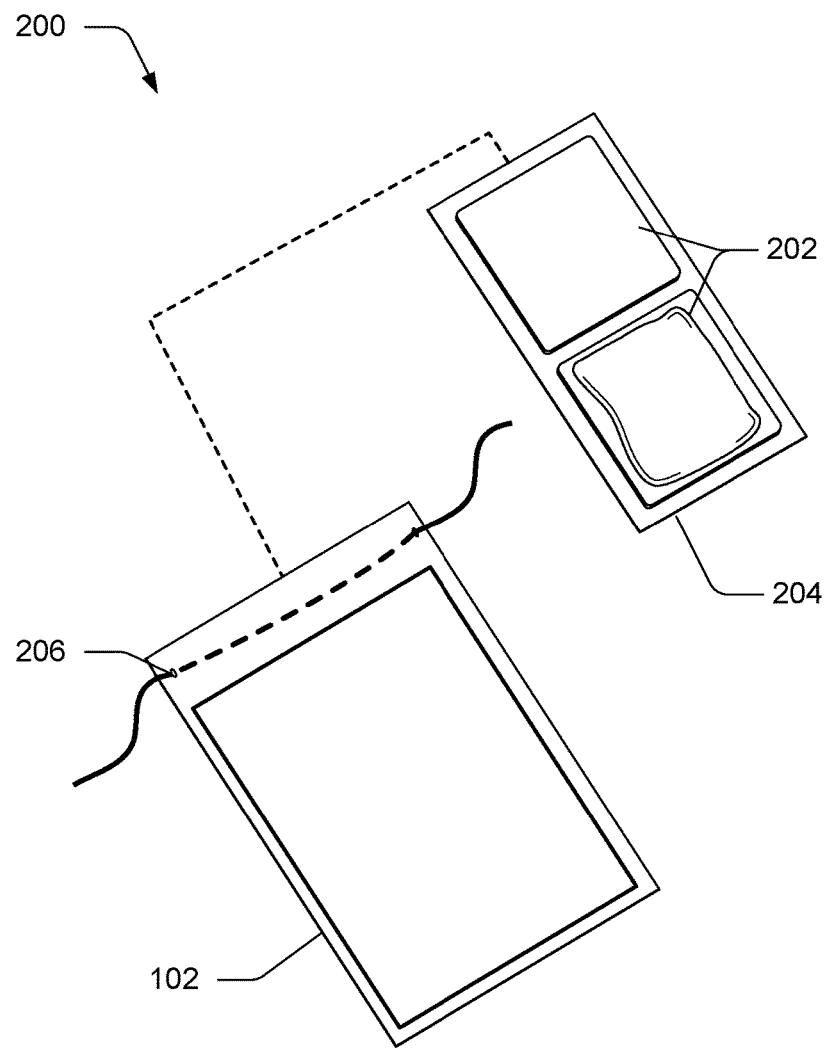
FIG. 2 illustrates another example portable medical device protector having a removable tray for storing one or more permeable applicators within an impermeable container.
Figure 3:
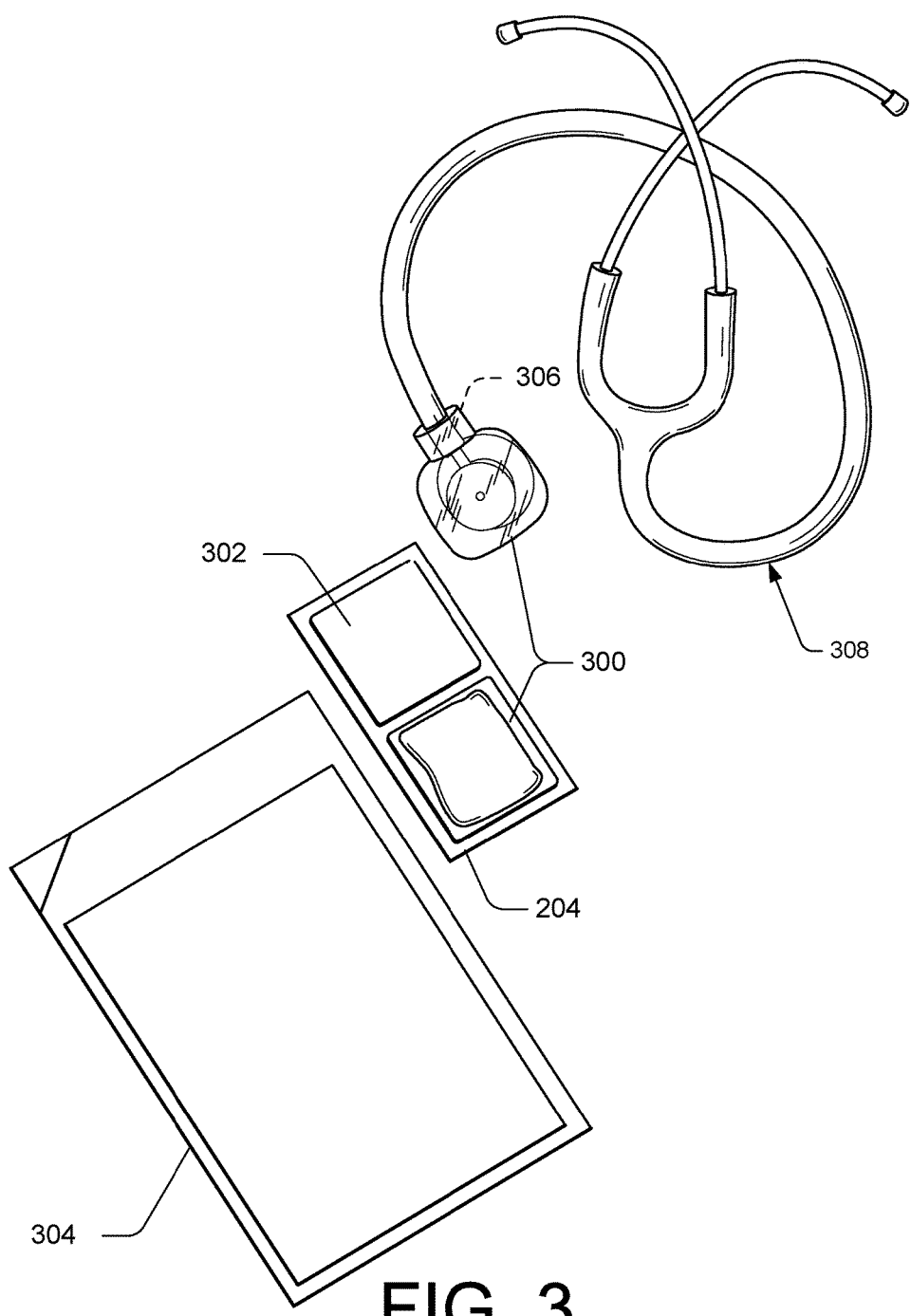
FIG. 3 illustrates another example portable medical device protector having a removable tray storing a permeable applicator for scrubbing a device (illustrated as a stethoscope) and an impermeable container for securing and preventing recontamination.

Various example protective devices are described herein. Described generally with reference to FIGS. 1-3 are example device protectors configured to prevent and/or reduce transmission of pathogenic organisms from one colonized patient, surface or user to another patient, surface or user.

FIG. 1 illustrates an example device protector 100 for use on a portable medical device. An example portable medical device include, but are not limited to, a stethoscope, a thermometer, a blood pressure monitor, a pulse oximeter, a nebulizer and associated equipment, a scope, a blood glucose monitor, a doppler, a capnograph, a suction pump, various equipment mouthpieces, diagnostic or therapeutic ultrasonic transducers and/or other diagnostic equipment. In one embodiment, an example device protector 100 may be configured to house any section of or an entire portable medical device and act as a protective cover. As illustrated in FIG. 1, the device protector 100 may contain an impermeable container 102 to house any section of or an entire portable medical device. The impermeable container 102 may be configured in any number of sizes designed to enclose any section or an entire portable medical device. For example, the impermeable container 102 may be configured to house the "bell" of a stethoscope or configured to house the entire stethoscope. Example materials for the composition of the impermeable container include, but are not limited to, polyethylene, aluminum oxide, aluminum foil, silicon oxide coated polymeric films, polypropylene, polysilicone, polytetrafluoroethylene, polyvinyl chloride, mylar, or combinations thereof.

In some embodiments, impermeable container 102 may include a closure mechanism 104 at the opening end 106 of the container 102 configured to securely enclose an inserted portion of the portable medical device. Example enclosure mechanisms may include, but are not limited to, a draw string, zip lock, foam opening, twist tie, plastic clip and/or a spring material.

In some embodiments, the closure mechanism is a draw string and/or twist tie. In these embodiments, the opening of the impermeable container may comprise a string, wire or other like material which has two ends extending from the impermeable container. The contents of the impermeable container (e.g., bell of the stethoscope) are enclosed when the ends of the string are pulled and/or twisted. Thus, closing the opening of the impermeable container.

In another embodiment, the closure mechanism on the impermeable container may be a foam opening. The foam opening may be configured to allow the portable medical device, or any part of thereof, to be inserted through the opening. Upon receipt of the portable medical device, the foam opening may revert back to its unopened position thereby protecting the portable medical device from contaminants located outside the impermeable container.

In another embodiment, the closure mechanism comprises a spring material. The spring material may hold the opening of the impermeable container in the closed position. The user may squeeze the opposing ends of the closure mechanism to activate the spring causing the opening of the impermeable container to open and become accessible to insertion of any portion of the portable medical device.

In some embodiments, a permeable applicator 108 may be stored within the impermeable container 102. The permeable applicator 108 may be impregnated or coated with an antimicrobial or antiseptic composition, such as the antimicrobial composition described in the preceding section. In some embodiments, the permeable applicator 108 may be removable from the impermeable container 102 and may be used to clean and/or disinfect any portion of the portable medical device (e.g., diaphragm, chestpiece, tubing, eartips, or any other part of a stethoscope).

Permeable applicator 108 may be configured in various shapes and size. For example, as illustrated in FIG. 1, applicator may be smaller than the impermeable container. In other embodiments, the applicator may be substantially the same size or larger than the impermeable container. In some embodiments, the applicator may be folded, doubled, tripled, etc. upon itself in any suitable manner to allow the applicator to fit within the impermeable container.

In another embodiment, the permeable applicator 108 may be attached as the interior lining of the impermeable container 102. For example, the permeable applicator may be removably or irremovably attached to the interior walls of the impermeable container. In this embodiment, a user may place the portable medical device, or any portion thereof, within the impermeable container. Once the device is inside the container, the user may manipulate the container by, for example, using a massaging action. Such action may allow the permeable applicator attached to the interior walls of the container to scrub/disinfect the medical device with the antimicrobial composition.

Example materials for the composition of the permeable applicator 108 include, but are not limited to, starch polymer, cellulosic gel, polyethylene foam, silicone open-cell foam, or mixtures thereof. In some embodiments, the permeable applicator 108 may include different surface treatments (e.g., siping, slitting, etc.), surface finishes (e.g., macro-, micro-, or nano-structures, etc.), and/or contours (e.g., rounded, ribbed, protrusions, fingers, etc.) to allow a user to grip the applicator and aid in scrubbing or cleaning the medical device.

FIG. 2 illustrates an alternative embodiment of a device protector 200, where one or more permeable applicator(s) 202 may be stored on a removable tray 204 that is located within the impermeable container 102. The tray 204 may be sealed within the impermeable container 102 prior to use by the user. In some embodiments, the tray 204 may be removed once the impermeable container 102 is opened allowing the user to access/use the one or more applicators 202. Tray 204 may be discarded prior to the placement of any part of the medical device within the impermeable container 102.

The one or more applicators 202 may have any of the features described above with regard to the permeable applicators of FIG. 1. In some embodiments, each of the one or more applicators on the tray may contain the same or different cleansing, antiseptic, or antimicrobial agent, or various concentrations thereof.

FIG. 2 illustrates an example draw string closure mechanism 206 as described above with reference to FIG. 1. However, in other embodiments, any of the other closure mechanism described above with reference to FIG. 1 may be used with the device protector 200.

Example materials for the composition of the tray 204 include, but are not limited to, polypropylene, high-density polyethylene, polytetrafluoroethylene, polyvinyl chloride, or any other suitable thermoplastic polymer. In some embodiments, tray 204 may be configured having one or more dividers to separate each portion storing the one or more permeable applicator(s) 202.

FIG. 3 illiterates yet another embodiment of a device protector. In this embodiment, an impermeable container 300 and a permeable applicator 302 may be located within a sterile, discardable package 304. As shown in FIG. 3, the impermeable container 300 (shown on both tray 204 and on the bell 306 of stethoscope 308) and the permeable applicator 302 may be located on tray 204 within the sterile packaging 304. Upon opening of the sterile package 304, the user may remove tray 204 and use the permeable applicator 302 that is impregnated with an antimicrobial or antiseptic composition to disinfect any part of the portable medical device, such as the stethoscope 308 illustrated in FIG. 3. After disinfecting the portable medical device with the applicator, the user may then place the portable medical device, or any portion thereof, within the impermeable container 300 to protect it from contamination. For example, as illustrated in FIG. 3, the impermeable container 300 would protect the bell 306 of the stethoscope 308 from coming into contact with one or contaminates when the user places the bell in a pocket, bag, or the like.

In some embodiments, the applicator located within the impermeable container or on a tray in the sterile package may be an applicator having an impermeable layer attached to a permeable, absorbent and/or adsorbent bottom layer thus, preventing an existing infectious agent on the user hand from transferring to the permeable bottom layer and the portable medical device.

Example Process

Figure 4:
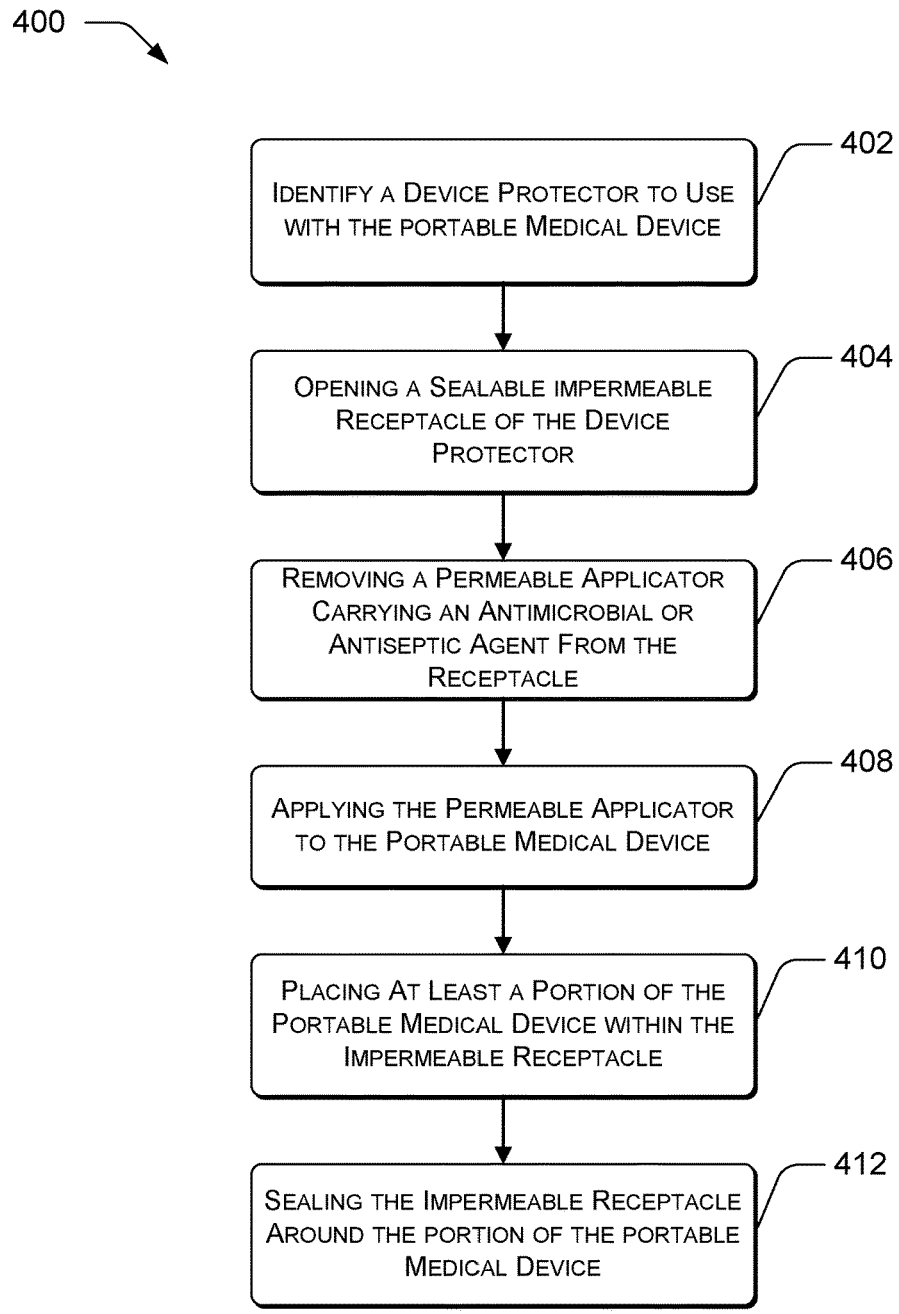
FIG. 4 is a flow diagram showing an example process for operating an example portable medical device protector.

FIG. 4 illustrates an example process 400 for execution of the techniques described above of operating an example protective device. The process 400 is illustrated as a logical flow graph. The order in which the operations are described is not intended to be construed as a limitation, and any number of the described operations can be combined in any order and/or in parallel to implement the process.

At operation 402, a device protector may be identified for use with a portable medical device. In the context of FIG. 3, if a user is traveling room to room in a hospital using a stethoscope, the user may identify a device protector to use with the stethoscope or bell of the stethoscope.

At operation 404, a sealable or resealable impermeable receptacle of the device protector may be opened. In the context of FIG. 1, a user may open the impermeable container by separating the closure mechanism 104 shown as a zip-lock mechanism.

At operation 406, a permeable applicator carrying an antimicrobial or antiseptic agent may be removed from the impermeable receptacle. Again in the context of FIG. 1, the permeable applicator 108 may be removable from the impermeable container 102.

At operation 408, the permeable applicator may be applied to at least a portion of the portable medical device. For example, the permeable applicator may be used to wipe or rub an entire stethoscope or any portion of the stethoscope (e.g., the bell).

At operation 410, at least a portion of the portable medical device may be placed within the impermeable receptacle of the device protector. In the context of FIG. 3, the bell 306 of the stethoscope 308 may be placed within impermeable container 300.

Finally at operation 412, the impermeable receptacle may be removably sealed around the inserted portion of the portable medical device. For example, the impermeable receptacle may be sealed by any of the mechanisms describe above with reference to FIGS. 1 and 2.

CONCLUSION

Although the disclosure describes embodiments having specific structural features and/or methodological acts, it is to be understood that the claims are not necessarily limited to the specific features or acts described. Rather, the specific features and acts are merely illustrative some embodiments that fall within the scope of the claims of the disclosure.

What is claimed is:

1. A portable medical device protector system comprising:
a sterile package housing a removable tray, the sterile package being sealed, the removable tray including:
an impermeable receptacle into which at least a portion of a portable medical device is insertable after removing the removable tray from the sterile package and extracting the impermeable receptacle from the removable tray, the impermeable receptacle being sealable and having a closure mechanism to close the impermeable receptacle around the portion of the portable medical device after insertion thereof,
a permeable applicator disposed on the removable tray or disposed in the impermeable receptacle included on the tray, the permeable applicator having a textured surface for scrubbing the portion of the portable medical device, and
a cleansing, antimicrobial or antiseptic agent carried by the permeable applicator, the cleansing, antimicrobial or antiseptic agent including:
water,
a low molecular weight alcohol,
a peroxide or peroxide-generating agent, and
a chelating agent.

2. The portable medical device protector system as recited in claim 1, wherein the removable tray includes a plurality of permeable applicators.

3. The portable medical device protector system as recited in claim 2, wherein each of the plurality of permeable applicators contains, respectively, a concentration amount of the antimicrobial or antiseptic agent different from other permeable applicators of the plurality of permeable applicators.

4. The portable medical device protector system as recited in claim 1, wherein the closure mechanism comprises a draw string, a zip-lock, a foam opening, a twist tie, a plastic clip, or a spring material to seal the sealable impermeable receptacle around the portion of the portable medical device.

5. The portable medical device protector system as recited in claim 1, wherein the sealable impermeable receptacle is sized to enclose the portable medical device entirely.

6. The portable medical device protector system as recited in claim 1, wherein:
   the chelating agent includes about 5 to about 50 mg/ml of ethylenediaminetetraacetic acid;
   the alcohol includes at most about 70% ethanol, by volume; and
   the peroxide or peroxide-generating agent includes at most about 7.5% hydrogen peroxide, by volume.

\* \* \* \* \*